United States Patent
Maurin et al.

(10) Patent No.: US 6,383,995 B1
(45) Date of Patent: May 7, 2002

(54) COMPOSITION FOR WASHING KERATIN MATERIALS, BASED ON A DETERGENT SURFACTANT, A POLYORGANOSILOXANE, A CATIONIC POLYMER AND A ACRYLIC TERPOLYMER

(75) Inventors: Veronique Maurin, Paris; Bernard Beauquey, Clichy, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/671,193

(22) Filed: Sep. 28, 2000

(30) Foreign Application Priority Data

Sep. 29, 1999 (FR) ............................................ 99 12164

(51) Int. Cl.$^7$ .............................. C11D 3/37; C11D 9/36
(52) U.S. Cl. ..................... 510/119; 510/121; 510/122; 510/123; 510/124; 510/125; 510/126; 510/127; 510/128; 510/130; 510/421; 510/422; 510/466; 510/477; 510/398
(58) Field of Search ................................ 510/119, 121, 510/122, 123, 124, 125, 126, 127, 128, 130, 421, 422, 466, 477, 398

(56) References Cited

U.S. PATENT DOCUMENTS 5,853,707 A    12/1998   Wells et al.  ............. 424/70.12

FOREIGN PATENT DOCUMENTS

| EP | 824914 | * | 2/1998 |
| EP | 0 825 200 |  | 2/1998 |
| WO | 92/10162 |  | 6/1992 |
| WO | 94/06403 | * | 3/1994 |

* cited by examiner

Primary Examiner—Charles Boyer
(74) Attorney, Agent, or Firm—Jacobson Holman, PLLC

(57) ABSTRACT

Composition for washing keratin materials, comprising, in a cosmetically acceptable medium:

i) at least one detergent surfactant;
ii) at least one polyorganosiloxane with a viscosity of less than 0.1 $m^2 \cdot s^{-1}$;
iii) at least one cationic polymer; and
iv) at least one acrylic terpolymer consisting of a monomer (a) chosen from a $C_1$–$C_6$ alkyl acrylate and a $C_1$–$C_6$ alkyl methacrylate; of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl(meth)acrylamide; of a monomer (c) chosen from a urethane produced by reaction between a monoethylenic unsaturated isocyanate and a nonionic surfactant, a copolymerizable ethylenic surfactant monomer, a surfactant monomer of urea type, an allyl ether containing alkylenoxy groups and a nonionic monomer of urethane type.

37 Claims, No Drawings

COMPOSITION FOR WASHING KERATIN MATERIALS, BASED ON A DETERGENT SURFACTANT, A POLYORGANOSILOXANE, A CATIONIC POLYMER AND A ACRYLIC TERPOLYMER

The present invention relates in general to compositions for washing keratin materials, based on a detergent surfactant, a polyorganosiloxane of specific viscosity, a cationic polymer and an acrylic terpolymer, as well as to a washing process using these compositions.

Polyorganosiloxanes are generally used in shampoo compositions as conditioners to improve the softness, feel and disentangling of the hair. However, it has been found that these polyorganosiloxanes lead to the formation of an aesthetically unpleasant layer at the surface of the shampoo, which users find undesirable. Stabilizers such as crosslinked acrylic polymers of the Carbopol type are frequently used to avoid the appearance of this phenomenon. However, these stabilizers have the drawback of reducing the cosmetic performance qualities of shampoos, in particular by making the hair coarser and more charged.

It is thus necessary to develop a detergent cosmetic composition containing polyorganosiloxanes, in particular a shampoo, which has a satisfactory aesthetic appearance while at the same time giving acceptable cosmetic performance qualities on keratin materials, i.e. in particular the hair and the scalp.

The Applicant has discovered, surprisingly, that it is possible to formulate compositions for washing keratin materials, in particular shampoos, having the desired properties, by using in these compositions a detergent surfactant, a polyorganosiloxane with a viscosity of less than $0.1\ m^2 \cdot s^{-1}$, a cationic polymer combined with a specific acrylic terpolymer, defined below. Specifically, it has been found that the use of the said acrylic terpolymer in the compositions of the present invention improves the stability of shampoos based on polyorganosiloxanes with a viscosity of less than $0.1\ m^2 \cdot s^{-1}$ while at the same time giving keratin materials, and in particular the hair, satisfactory cosmetic properties, particularly as regards the disentangling, suppleness, manageability and body.

It has also been found that the compositions of the invention have good skin tolerance.

A subject of the invention is thus compositions for washing keratin materials, essentially characterized in that they comprise, in a cosmetically acceptable medium:

i) at least one detergent surfactant;
ii) at least one polyorganosiloxane with a viscosity of less than $0.1\ m^2 \cdot s^{-1}$;
iii) at least one cationic polymer; and
iv) at least one acrylic terpolymer consisting of:
   from 5% to 80% by weight, preferably from 15% to 70% by weight and more preferably from 40% to 70% by weight, of an acrylate monomer (a) chosen from a $C_1$–$C_6$ alkyl acrylate and a $C_1$–$C_6$ alkyl methacrylate;
   from 5% to 80% by weight, preferably from 10% to 70% by weight and more preferably from 20% to 60% by weight, of a monomer (b) chosen from a heterocyclic vinyl compound containing at least one nitrogen or sulphur atom, a (meth) acrylamide, mono- or di($C_1$–$C_4$)alkylamino($C_1$–$C_4$)alkyl (meth)acrylate and a mono- or di($C_1$–$C_4$)alkylamino ($C_1$–$C_4$)alkyl(meth)acrylamide;
   from 0.1% to 30% by weight, preferably from 0.1% to 10% by weight, of a monomer (c) chosen from:
      a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
      a copolymerizable ethylenic unsaturated surfactant monomer obtained by condensing a nonionic surfactant with an $\alpha,\beta$-ethylenic unsaturated carboxylic acid or its anhydride;
      a surfactant monomer chosen from reaction products such as urea of a monoethylenic unsaturated mono-isocyanate with a nonionic surfactant containing an amine function;
      a (meth)allyl ether of formula $CH_2 = CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200 and preferably less than or equal to 100, m and p denote zero or an integer less than n and $R_2$ is a hydrophobic group of at least 8 carbon atoms and preferably of $C_8$–$C_{30}$; and
      a nonionic monomer such as urethane produced by reaction of a monohydric nonionic surfactant with a monoethylenic unsaturated isocyanate;
         the weight percentages of monomers being based on the total weight of the monomers constituting the terpolymer.

In the washing composition of the invention, the acrylic terpolymer is present in a proportion of from 0.01% to 20% by weight of active material (A.M.), preferably 0.1% to 10% by weight, relative to the total weight of the composition.

Preferred acrylate monomers (a) in particular comprise $C_2$–$C_6$ alkyl acrylates. Ethyl acrylate is most particularly preferred.

Examples of preferred monomers (b) which may be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide. N,N-Dimethylaminoethyl methacrylate is most particularly preferred.

The preferred monomers (c) are the copolymerizable ethylenic unsaturated surfactant monomers obtained by condensing a nonionic surfactant with an $\alpha,\beta$-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$–$C_{30}$ fatty alcohols alkoxylated with 2 to 100 mol and preferably from 5 to 50 mol of an alkylene oxide, such as, for example, polyethylene glycol ethers of $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structures® Plus>> polymer sold by the company National Starch, which consists of acrylates, amino(meth) acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylates, polyethylene glycol dimethacrylates, penta- and tetraacrylates, triallyl pentaerythritols, octaallyl sucroses, cycloparaffins, cycloolefins and N-methylenebisacrylamide.

The viscosity is preferably measured by capillary viscometry, for example using a capillary viscometer, in particular an Ubbelohde viscometer at a temperature of 25° C., according to ASTM standard D445-97. The so-called falling-ball method can also be used.

In the context of the present invention, the expression <<polyorganosiloxanes with a viscosity of less than 0.1 $m^2 \cdot s^{-1}$>> means modified or unmodified polyorganosiloxanes, i.e. polyorganosiloxane oils in native form or in the form of solutions in organic solvents or alternatively in the form of emulsions or microemulsions. The silicones preferably have a viscosity of between 0.001 and 0.08 $m^2 \cdot s^{-1}$ and more particularly between 0.01 and 0.08 $m^2 \cdot s^{-1}$.

Among the polyorganosiloxanes which can be used in accordance with the present invention, mention may be made, in a non-limiting manner, of:

I. Volatile silicones: these have a boiling point of between 60° C. and 260° C. They are chosen from cyclic silicones containing from 3 to 7 and preferably 4 to 5 silicon atoms. Examples of these silicones are octamethylcyclotetrasiloxane sold under the name <<Volatile Silicone 7207>> by Union Carbide or <<Silbione 70045 V2>> by Rhône Poulenc, decamethylcyclopentasiloxane sold under the name <<Volatile Silicone 7158>> by Union Carbide and <<Silbione 70045 V5>> by Rhône Poulenc, as well as mixtures thereof. Mention is also made of cyclocopolymers of the dimethylsiloxane/methylalkylsiloxane type, such as <<Volatile Silicone FZ3109>> sold by the company Union Carbide, which is a dimethylsiloxane/methyloctylsiloxane cyclocopolymer.

II. Non-volatile silicones: these consist mainly of:
(i) polyalkylsiloxanes; among the polyalkylsiloxanes which may mainly be mentioned are linear polydimethylsiloxanes containing trimethylsilyl end groups, such as, for example, and in a non-limiting manner, the <<Silbione>> oils of the 70047 series sold by Rhodia Chimie; the DC 200 polydimethylsiloxanes with a viscosity of 0.03 to 0.06 $m^2 \cdot s^{-1}$ from Dow Corning;
(ii) polyarylsiloxanes;
(iii) polyalkylarylsiloxanes; mention may be made of linear and branched polymethylphenylsiloxanes, polydimethylmethylphenylsiloxanes and polydimethyldiphenylsiloxanes, such as, for example, the oil <<Rhodorsil 763>> from Rhodia Chimie;
(iv) organomodified polyorganosiloxanes; i.e. silicones as defined above, comprising in their general structure one or more organofunctional groups directly linked to the siloxane chain or linked via a hydrocarbon-based radical; mention is made, for example, of silicones comprising:
  a) polyethylenoxy and/or polypropylenoxy groups optionally comprising alkyl groups, such as the product known as dimethicone copolyol sold by the company Dow Corning under the name <<DC 1248>> and the alkyl (C12) methicone copolyol sold by the company Dow Corning under the name <<Q2 5200>>;
  b) (per)fluoro groups, such as trifluoroalkyl groups, such as, for example, those sold by the company General Electric under the name <<FF.150 Fluorosilicone Fluid>>;
  c) hydroxyacylamino groups, such as those described in European patent application EP-A-0 342 834 and in particular the silicone sold by the company Dow Corning under the name <<Q2-8413>>;
  d) thiol groups, such as in the silicones <<X 2-8360>>from Dow Corning or <<GP 72A>> and <<GP 71>> from Genesee;
  e) substituted or unsubstituted amine groups, such as the products sold under the name GP 4 Silicone Fluid and GP 7100 by the company Genesee or the products sold under the names Q2 8220 and Dow Corning 929 or 939 by the company Dow Corning. The substituted amine groups are, in particular, $C_1$–$C_4$ aminoalkyl or amino($C_1$–$C_4$)alkylamino($C_1$–$C_4$) alkyl groups. The silicones known as amodimethicone and trimethylsilylamodimethicone according to the CTFA name (1997) are used more particularly;
  f) carboxylate groups, such as the products described in European patent EP 186 507 from Chisso Corporation;
  g) hydroxyl groups, such as the polyorganosiloxanes containing a hydroxyalkyl function, which are described in patent application FR-A-2 589 476;
  h) alkoxy groups containing at least 12 carbon atoms, such as the product <<Silicone Copolymer F 755>> from SWS Silicones;
  i) acyloxyalkyl groups containing at least 12 carbon atoms, such as, for example, the polyorganosiloxanes described in patent application FR-A-2 641 185;
  j) quaternary ammonium groups, such as in the product <<Abil K 3270>> from the company Goldschmidt;
  k) amphoteric or betaine groups, such as in the product sold by the company Goldschmidt under the name <<Abil B 9950>>;
  l) bisulphite groups, such as in the products sold by the company Goldschmidt under the names <<Abil S 201>>and <<Abil S 255>>;
(v) block copolymers containing a linear polysiloxane-polyalkylene block as repeating unit; the preparation of such block copolymers used in the context of the present invention is described in European patent application EP 0 492 657 A1, the teaching of which is included in the present description by way of reference;

(vi) grafted silicone polymers, containing a non-silicone organic skeleton, consisting of a main organic chain formed from organic monomers containing no silicone, onto which is grafted, inside the said chain as well as, optionally, on at least one of its ends, at least one polysiloxane macromonomer; in particular those chosen more preferably from those described in U.S. Pat. Nos. 4,963,935, 4,728,571 and 4,972,037 and patent applications EP-A-0 412 704, EP-A-0 412 707, EP-A-0 640 105 and WO 95/00578, the teachings of which are included in their entirety into the present description by way of non-limiting references;

(vii) grafted silicone polymers, containing a polysiloxane skeleton grafted with non-silicone organic monomers, comprising a main polysiloxane chain onto which is grafted, within the said chain as well as, optionally, on at least one of its ends, at least one organic macromonomer containing no silicone; examples of such polymers, as well as the particular method for preparing them, are described in particular in patent applications EP-A-0 582 152, WO 93/23009 and WO 95/03776, the teachings of which are included in their entirety into the present description by way of non-limiting references;

(viii) or mixtures thereof.

The polyorganosiloxanes preferably used according to the invention are the non-volatile polyorganopolysiloxanes and, in particular, the aminated or non-aminated polydimethylsiloxanes.

The polyorganosiloxanes with a viscosity of less than 0.1 $m^2 \cdot s^{-1}$ may be present in proportions of between 0.01% and 20% by weight relative to the total weight of the composition and preferably in proportions of between 0.1% and 10% by weight relative to the total weight of the composition.

As mentioned previously, the compositions according to the invention contain at least one detergent surfactant, chosen in particular from anionic, amphoteric, nonionic and cationic surfactants with detergent properties, and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamidephosuccinates; alkyl sulphosuccinates; alkyl sulphoacetates; alkyl phosphates, alkyl ether phosphates; acyl sarcosinates, acyl isethionates and N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of sorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; $(C_8-C_{20})$ alkylbetaines, sulphobetaines, $(C_8-C_{20})$alkylamido$(C_1-C_6)$alkylbetaines or $(C_8-C_{20})$ alkylamido $(C_1-C_6)$alkylsulphobetaines.

Among the amine derivatives which may be mentioned are the products sold under the name Miranol, such as those described in U.S. Pat. Nos. 2,528,378 and 2,781,354 and classified in the CTFA dictionary, 7th edition, 1997, under the name Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Capryloamphodipropionate, Lauroamphodipropionate acid, Cocoamphodipropionate acid.

The cationic surfactants are chosen in particular from salts of optionally polyoxyalkylenated primary, secondary or tertiary fatty amines; quaternary ammonium salts; imidazoline derivatives; or amine oxides of cationic nature.

The preferred quaternary ammonium salts are tetraalkylammonium halides (for example chlorides) such as, for example, dialkyldimethylammonium or alkyltrimethylammonium chlorides, in which the alkyl radical contains from about 12 to 22 carbon atoms, in particular behenyltrimethylammonium chloride, distearyldimethylammonium chloride, cetyltrimethylammonium chloride, benzyldimethylstearylammonium chloride or stearamidopropyldimethyl (myristyl acetate)ammonium chloride sold under the name <<Cepharyl 70>> by the company Van Dyk.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular) can also be used. The acyl radicals preferably contain 14 to 18 carbon atoms and are obtained more particularly from a plant oil such as palm oil or sunflower oil.

The surfactants are used in the compositions in accordance with the invention in proportions that are sufficient to give the composition a detergent nature, generally in a proportion of at least 4% by weight and preferably between 5% and 50% by weight relative to the total weight of the composition, and in particular between 8% and 35%.

The compositions of the invention also contain at least one cationic polymer chosen from all those already known per se, in particular those described in patent application EP-A-0 337 354 and in French patent applications FR-A-2 270 846, 2 383 660, 2 598 611, 2 470 596 and 2 519 863.

The cationic polymers used generally have a molecular mass of between 500 and 5 $10^6$ approximately and preferably between 103 and 3 $10^6$ approximately.

Among the cationic polymers which may be mentioned are quaternized proteins (or protein hydrolysates) and polymers of the polyamine, polyaminoamide and polyquaternary ammonium type. These are known products.

The quaternized proteins or protein hydrolysates are in particular chemically modified polypeptides bearing quaternary ammonium groups at the end of a chain, or grafted onto this chain. Their molecular mass can vary, for example, from 1500 to 10,000, and in particular from 2000 to 5000 approximately. Among these compounds, mention may be made in particular of:

collagen hydrolysates bearing triethylammonium groups, such as the products known in the CTFA dictionary as <<Triethonium Hydrolysed Collagen Ethosulphate>>;

collagen hydrolysates bearing trimethylammonium chloride and trimethylstearylammonium chloride groups, which are known in the CTFA dictionary as <<Steartrimonium Hydrolysed Collagen>>;

protein hydrolysates bearing on the polypeptide chain quaternary ammonium groups comprising at least one alkyl radical containing from 1 to 18 carbon atoms.

Among these protein hydrolysates which may be mentioned, inter alia, are <<Croquat L>>, <<Croquat M>>, <<Croquat S>> and <<Crotein Q>> sold by the company Croda.

Other quaternized proteins or hydrolysates are, for example, those sold by the company Inolex, under the name <<Lexein QX 3000>>.

Mention may also be made of quaternized plant proteins such as wheat, corn or soybean proteins: quaternized wheat proteins which may be mentioned are those known in the CTFA dictionary as <<Cocodimonium Hydrolysed Wheat Protein>>, <<Lauridimonium Hydrolysed Wheat Protein>> or <<Steardimonium Hydrolysed Wheat Protein>>.

The polymers of the polyamine, polyaminoamide or polyquaternary ammonium type which may be used in accordance with the present invention and which may be mentioned in particular are those described in French patents Nos. 2 505 348 and 2 542 997. Among these polymers, mention may be made of:

(1) Quaternized or non-quaternized vinylpyrrolidone/ dialkylaminoalkyl acrylate or methacrylate copolymers, such as the polymers described in detail in French patents 2 077 143 and 2 393 573.

(2) Cellulose ether derivatives comprising quaternary ammonium groups, described in French patent 1 492 597.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

(4) Polysaccharides and in particular cationic guar gums described more particularly in U.S. Pat. Nos. 3,589,578 and 4,031,307.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2 162 025 and 2 280 361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are described in particular in French patents 2 252 840 and 2 368 508.

(7) Polyaminoamide derivatives resulting from the condensation of polyalkylene polyamines with polycarboxylic acids followed by an alkylation with bifunctional agents. Mention may be made, for example, of adipic acid/ dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

(8) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, the molar ratio between the polyalkylene polyamine and the dicarboxylic acid being between 0.8:1 and 1.4:1, the polyaminoamide resulting therefrom being reacted with the epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

(9) Cyclopolymers of methyldiallylamine or of dimethyldiallylammonium, in particular those described in French patent 2 080 759 and in its Certificate of Addition 2 190 406.

(10) The diquaternary ammonium polymers described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The polyquaternary ammonium polymers described in particular in patent application EP-A-122 324.

(12) Homopolymers or copolymers derived from acrylic or methacrylic acids and comprising $CH_2$—$CHR_a$—CO—O—$A_1$—$NR_eR_f$, $CH_2$—$CHR_a$—CO—O—$A_1$—$N^+R_bR_cR_d$, $X^-$ and/or $CH_2$—$CHR_a$—CO—NH—$A_1$—$N^+R_bR_cR_d$, $X^-$ units, in which the groups $R_a$ independently denote H or $CH_3$, the groups $A_1$ independently denote a linear or branched alkyl group of 1 to 6 carbon atoms or a hydroxyalkyl group of 1 to 4 carbon atoms, the groups $R_b$, $R_c$ and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, X⁻ denotes an anion, for example methosulphate or halide, such as chloride or bromide

(13) Quaternary polymers of vinylpyrrolidone and of vinylimidazole such as, for example, the products sold under the names <<Luviquat FC 905>>, <<Luviquat FC 550>> and <<Luviquat FC 370>> by the company BASF.

(14) The polyamines such as <<Polyquart H>> sold by Henkel, referred to under the name <<Polyethylene Glycol Tallow Polyamine>> in the CTFA dictionary.

(15) Crosslinked polymers of methacryloyloxyethyltrimethylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by a crosslinking with a compound containing olefinic unsaturation, in particular methylenebisacrylamide. An acrylamide/methacryloyloxyethyltrimethylammonium chloride crosslinked copolymer (20/80 by weight) in the form of a dispersion containing 50% by weight of the said copolymer in mineral oil can more particularly be used.

Other cationic polymers which can be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers which can be used in the context of the present invention, cellulose ether derivatives comprising quaternary ammonium groups, polysaccharides and in particular cationic guar gum and cyclopolymers of methyldiallylamine or of dimethyldiallylammonium are preferred.

The cationic polymers are used in the compositions of the invention in proportions of between 0.001% and 20% by weight and preferably between 0.05% and 5% by weight, relative to the total weight of the composition.

The compositions according to the invention have a pH generally of between 3 and 12 and more particularly between 4 and 8.

The cosmetically acceptable medium for the compositions consists either of water or of one or more solvents, or of a mixture of water and at least one solvent chosen from lower alcohols, alkylene glycols and polyol ethers.

The cosmetic performance qualities of the compositions according to the invention can be improved by adding polyorganosiloxanes other than the polyalkylsiloxanes described above, with a viscosity of greater than $0.1\ m^2 \cdot s$, and in particular silicone resins or gums.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, menthol, nicotinate derivatives, agents for preventing hair loss, antidandruff agents, foam stabilizers, propellants, screening agents, dyes, ceramides, vitamins or provitamins, acidifying or basifying agents or other well-known cosmetic adjuvants.

In one preferred embodiment of the invention, the compositions according to the invention are used as shampoos for washing the hair.

The process for washing keratin materials consists in applying a composition as defined above to wet or dry keratin materials in amounts that are effective to wash them, this application being followed by rinsing after an optional period of leaving the composition to stand on the keratin materials.

The example which follows is intended to illustrate the invention.

| SHAMPOO EXAMPLE | |
|---|---|
| Propylene glycol | 0.1 g |
| Sodium N-cocoylamidoethyl-N-ethoxycarboxymethyl glycinate containing 38% A.M., sold under the name <<Miranol C2M Concentration>> by the company Rhodia | 8 g |
| Hydroxypropyl guar trimethyl ammonium chloride sold under the name <<Jaguar C13S>> by the company Meyhall | 0.2 g |
| 1-(Hexadecyloxy)-2-octadecanol/cetyl alcohol mixture | 2.5 g |
| Coconut acid monoisopropanolamide | 0.5 g |
| Sodium lauryl ether sulphate (2.2 EO) containing 70% A.M. | 22 g |
| Polydimethylsiloxane with a viscosity of 0.06 $m^2 \cdot s^{-1}$, sold under the name <<DC 200 Fluid - 60,000 cSt>> by the company Dow Corning | 2.7 g |
| Terpolymer of acrylates, amino(meth)acrylates and $C_{10}$—$C_{30}$ alkyl itaconate, polyoxyethylenated with 20 mol of ethylene oxide, as an aqueous dispersion containing 20% A.M., sold under the name <<Structure ® Plus>> by the company National Starch | 1 g |
| Fragrance, preserving agents    qs | |
| Sterilized demineralized water    qs | 100 g |

The pH is adjusted to 7.5 with citric acid or sodium hydroxide.

After applying this shampoo, dried hair is found to have suppleness, manageability and body.

The hair is also easy to disentangle.

What is claimed is:

1. A composition for washing keratin materials comprising
    at least one detergent surfactant,
    at least one cationic polymer,
    at least one polyorganosiloxane oil with a viscosity of less than or equal to $0.1\ m^2 \cdot s^{-1}$, and at least one acrylic terpolymer containing, in amounts based on the total weight of the monomers constituting the terpolymer:
        an acrylate monomer (a) from 5% to 80% by weight selected from the group consisting of a $C_1$–$C_6$ alkyl acrylate and a $C_1$–$C_6$ alkyl methacrylate;
        a monomer (b) from 5% to 80% by weight selected from the group consisting of a heterocyclic vinyl compound containing at least one nitrogen or sulphur atom, a (meth)acrylamide, a mono- or di($C_1$–$C_4$)alkylamino($C_1$–$C_4$)alkyl(meth)acrylate and a mono- or di ($C_1$–$C_4$)alkylamino($C_1$–$C_4$)alkyl (meth)acrylamide;
        a monomer (c) from 0.1% to 30% by weight selected from the group consisting of:
            i) a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
            ii) a copolymerizable ethylenic unsaturated surfactant monomer obtained by condensing a nonionic surfactant with an α,β-ethylenic unsaturated carboxylic acid or its anhydride;
            iii) a surfactant monomer of urea produced by reacting a monoethylenic unsaturated monoisocyanate with a nonionic surfactant containing an amine function;

iv) a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200, m and p denote zero or an integer less than n and $R_2$ is a hydrophobic group of at least 8 carbon atoms; and v) a nonionic urethane monomer produced by reacting a monohydric nonionic surfactant with a monoethylenic unsaturated isocyanate;

in a cosmetically acceptable medium.

2. The composition according to claim 1, wherein the terpolymer is present in a proportion of 0.01% to 20% by weight relative to the total weight of the composition.

3. The composition according to claim 1, wherein the monomer (a) is a $C_2-C_6$ alkyl acrylate.

4. The composition according to claim 1, wherein the monomer (b) is selected from the group consisting of N,N-dimethylaminoethyl methacrylate, N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino(meth)acrylates and $C_{10}-C_{30}$ alkyl itaconate polyoxyethylenated with 20 mol of ethylene oxide.

7. The composition according to claim 1, wherein the acrylic terpolymer further includes a crosslinking monomer.

8. The composition according to claim 1, wherein the polyorganosiloxane with a viscosity of less than 0.1 $m^2 \cdot s^{-1}$ is selected from the group consisting of:
(i) polyalkylsiloxanes;
(ii) polyarylsiloxanes;
(iii) polyalkylarylsiloxanes;
(iv) organomodified polyorganosiloxanes;
(v) block copolymers containing a polysiloxane-polyalkylene block as repeating unit;
(vi) grafted silicone polymers, containing a non-silicone organic skeleton;
(vii) grafted silicone polymers, containing a polysiloxane skeleton grafted with non-silicone organic monomers;
(viii) and mixtures thereof.

9. The composition according to claim 1, wherein the polyorganosiloxane with a viscosity of less than 0.1 $m^2 \cdot s^{-1}$ is a polydimethylsiloxane.

10. The composition according to claim 1, wherein the polyorganosiloxane with a viscosity of less than 0.1 $m^2 \cdot s^{-1}$ is present in a proportion of 0.01% to 20% by weight relative to the total weight of the composition.

11. The composition according to claim 1, wherein the detergent surfactant is chosen from anionic, amphoteric, nonionic and cationic surfactants, and mixtures thereof.

12. The composition according to claim 11, wherein the anionic surfactants are selected from the group consisting of alkaline salts, magnesium salts, ammonium salts, amine salts and amino alcohol salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates;
wherein the alkyl or acyl radical comprises a carbon-based chain containing from 8 to 30 carbon atoms;
fatty acid salts of oleic, ricinoleic, palmitic and stearic acid; coconut oil acid or hydrogenated coconut oil acid; acyl lactylates, wherein the acyl radical contains from 8 to 30 carbon atoms;
alkyl D-galactosiduronic acids and salts thereof, polyoxyalkylenated alkyl or alkylaryl ether carboxylic acids or salts thereof, and polyoxyalkylenated alkylamido ether carboxylic acids or salts thereof.

13. The composition according to claim 11, wherein the nonionic surfactants are selected from the group consisting of: polyethoxylated, polyoxypropylenated or polyglycerolated fatty acids or alkylphenols or alcohols having a fatty chain containing 8 to 30 carbon atoms, having between 2 and 50 ethylene oxide or propylene oxide groups and having between 2 and 30 glycerol groups; copolymers of ethylene oxide and propylene oxide; condensates of ethylene oxide and of propylene oxide with fatty alcohols; polyethoxylated fatty amides; polyglycerolated fatty amides; polyethoxylated fatty amines; oxyethylenated fatty acid esters of sorbitan; fatty acid esters of sucrose, fatty acid esters of polyethylene glycol; alkylpolyglycosides; and carbamate or amide derivatives of N-alkylglucamines, aldobionamides, or amine oxides.

14. The composition according to claim 11, wherein the amphoteric surfactants are selected from the group consisting of secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; and $(C_8-C_{20})$ alkylbetaines, sulphobetaines, $(C_8-C_{20})$alkylamido$(C_1-C_6)$ alkylbetaines or $(C_8-C_{20})$alkylamido$(C_1-C_6)$ alkylsulphobetaines.

15. The composition according to claim 11, wherein the cationic surfactants are selected from the group consisting of: salts of polyoxyalkylenated primary, secondary or tertiary fatty amines; quaternary ammonium salts; imidazoline derivatives; and amine oxides of cationic nature.

16. The composition according to claim 1, wherein the detergent surfactant is present in a proportion of at least 4% by weight relative to the total weight of the composition.

17. The composition according to claim 1, wherein the cationic polymer is selected from the group consisting of:
proteins or protein hydrolysates, collagen hydrolysates bearing trimethylammonium chloride and trimethylstearylammonium chloride groups, protein hydrolysates bearing on the polypeptide chain quaternary ammonium groups comprising at least one alkyl radical containing from 1 to 18 carbon atoms, and quaternized plant proteins;
polymers of the polyamine, polyaminoamide or polyquaternary ammonium type selected from the group consisting of:
i) quaternized or non-quaternized vinylpyrrolidone/dialkylaminoalkyl acrylate or methacrylate copolymers,
ii) cellulose ether derivatives comprising quaternary ammonium groups, iii) cationic cellulose derivatives,
iv) cationic polysaccharides,
v) polymers consisting of piperazinyl units and of divalent alkylene or hydroxyalkylene radicals containing straight or branched chains,
vi) water-soluble polyaminoamides,
vii) polyaminoamide derivatives resulting from the condensation of polyalkylene polyamines with polycarboxylic acids followed by an alkylation with bifunctional agents,
viii) polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms,
ix) cyclopolymers of methyldiallylamine or dimethyldiallylammonium,
x) diquaternary ammonium polymers,
xi) polyquaternary ammonium polymers,
xii) homopolymers or copolymers derived from acrylic or methacrylic acids and comprising
$CH_2$—$CHR_a$—CO—O—$A_1$—$NR_eR_f$, $CH_2$—$CHR_a$—CO—O—$A_1$—$N^+R_bR_cR_d$, $X^-$ and/or $CH_2$—$CHR_a$—CO—NH—$A_1$—$N^+R_bR_cR_d$, $X^-$ units,
wherein the groups $R_a$ independently denote H or $CH_3$, the groups $A_1$ independently denote a linear or branched alkylene group of 1 to 6 carbon atoms or a hydroxyalkylene group of 1 to 4 carbon atoms, the groups $R_b$, $R_c$ and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, $X^-$ denotes an anion, for example methosulphate or halide, such as chloride or bromide,
xiii) quaternary polymers of vinylpyrrolidone and of vinylimidazole,
xiv) polyamines referred to under the name "Polyethylene Glycol Tallow Polyamine" in the CTFA dictionary,
xv) crosslinked polymers of methacryloyloxyethyltrimethylammonium salt,
polyalkyleneimines, polymers containing vinylpyridine or vinylpyridinium units, condensates of polyamines and of epichlorohydrin, polyquaternary ureylenes and chitin derivatives.

18. The composition according to claim 1, wherein the cationic polymer is selected from the group consisting of cellulose ether derivatives comprising quaternary ammonium groups, cationic guar gums and cyclopolymers of methyldiallylamine or dimethyldiallylammonium.

19. The composition according to claim 1, wherein the cationic polymer is present in a proportion of 0.001% and 20% by weight relative to the total weight of the composition.

20. The composition according to claim 1, wherein the composition has a pH of between 3 and 12.

21. The composition according to claim 1, wherein the cosmetically acceptable medium is water, one or more solvents or of a mixture of water and at least one solvent selected from the group consisting of lower alcohols, alkylene glycols and polyol ethers.

22. The composition according to claim 1, wherein the composition also contains at least one silicone resin or gum.

23. The composition according to claim 1, and further comprising at least one cosmetically acceptable adjuvant selected from the group consisting of fragrances, preserving agents, sequestering agents, wetting agents, sugars, plant, animal, mineral or synthetic oils, amphoteric polymers, menthol, nicotinate derivatives, agents for preventing hair loss, antidandruff agents, foam stabilizers, propellants, dyes, screening agents, ceramides, vitamins or provitamins and acidifying or basifying agents.

24. A shampoo comprising the composition as defined in claim 1.

25. A method for washing keratin materials comprising applying at least one composition as defined in claim 1 to wet or dry keratin materials and rinsing with water.

26. The composition according to claim 1, wherein the acrylate monomer (a) is in an amount of 15% to 70% by weight.

27. The composition according to claim 1, wherein the acrylate monomer (a) is in an amount of 40% to 70% by weight.

28. The composition according to claim 1, wherein the monomer (b) is in an amount of 10% to 70% by weight.

29. The composition according to claim 1, wherein the monomer (b) is in an amount of 20% to 60% by weight.

30. The composition according to claim 1, wherein the monomer (c) is in an amount of 0.1% to 10% by weight.

31. The composition according to claim 1, wherein the terpolymer is present in a proportion of 0.1% to 10% by weight relative to the total weight of the composition.

32. The composition according to claim 1, wherein the polyorganosiloxane is present in a proportion of 0.1% to 10% by weight relative to the total weight of the composition.

33. The composition according to claim 1, wherein the detergent surfactant is present in a proportion of 5% to 50% by weight relative to the total weight of the composition.

34. The composition according to claim 1, wherein the detergent surfactant is present in a proportion of 8% to 35% by weight relative to the total weight of the composition.

35. The composition according to claim 1, wherein the composition has a pH of between 4 and 8.

36. The composition according to claim 1, wherein the composition contains a cationic polymer in proportions of between 0.05% and 5% by weight relative to the total weight of the composition.

37. The method for washing keratin materials according to claim 25, and further comprising allowing the composition to stand on the keratin materials for a period of time.

* * * * *